(12) United States Patent
Mather et al.

(10) Patent No.: US 9,039,773 B2
(45) Date of Patent: May 26, 2015

(54) INTERVERTEBRAL IMPLANT FACILITATING UNILATERAL PLACEMENT, INSTRUMENTS AND METHODS

(75) Inventors: Steven E. Mather, Hillsdale, IL (US); Wagdy W. Asaad, Burr Ridge, IL (US)

(73) Assignee: SpineCraft, LLC, Westmont, IL (US)

( * ) Notice: Subject to any disclaimer, the term of this patent is extended or adjusted under 35 U.S.C. 154(b) by 418 days.

(21) Appl. No.: 13/531,511

(22) Filed: Jun. 23, 2012

(65) Prior Publication Data

US 2012/0265311 A1 Oct. 18, 2012

Related U.S. Application Data

(62) Division of application No. 12/792,040, filed on Jun. 2, 2010.

(51) Int. Cl.
*A61F 2/44* (2006.01)
*A61F 2/46* (2006.01)
*A61F 2/30* (2006.01)
*A61F 2/28* (2006.01)

(52) U.S. Cl.
CPC .......... *A61F 2/447* (2013.01); *A61F 2/30965* (2013.01); *A61F 2/4611* (2013.01); *A61F 2002/2817* (2013.01); *A61F 2002/2835* (2013.01); *A61F 2002/30062* (2013.01); *A61F 2002/3008* (2013.01); *A61F 2002/30538* (2013.01); *A61F 2002/3082* (2013.01); *A61F 2002/30841* (2013.01); *A61F 2002/30892* (2013.01); *A61F 2002/4475* (2013.01); *A61F 2002/448* (2013.01); *A61F 2002/4628* (2013.01); *A61F 2002/4629* (2013.01); *A61F 2310/00017* (2013.01); *A61F 2310/00023* (2013.01); *A61F 2310/00293* (2013.01)

(58) Field of Classification Search
USPC ....................................... 623/17.16
See application file for complete search history.

(56) References Cited

U.S. PATENT DOCUMENTS

| | | | |
|---|---|---|---|
| 4,645,505 A | 2/1987 | Swanson | |
| 4,772,287 A * | 9/1988 | Ray et al. | 623/17.12 |
| 6,277,149 B1 | 8/2001 | Boyle et al. | |
| 6,595,998 B2 | 7/2003 | Johnson et al. | |
| 6,761,739 B2 | 7/2004 | Shepard | |
| 2003/0139813 A1 * | 7/2003 | Messerli et al. | 623/17.11 |
| 2003/0149483 A1 * | 8/2003 | Michelson | 623/17.11 |
| 2005/0203538 A1 | 9/2005 | Lo et al. | |
| 2006/0247783 A1 * | 11/2006 | McKay | 623/17.16 |
| 2008/0021559 A1 * | 1/2008 | Thramann | 623/17.16 |
| 2008/0132901 A1 * | 6/2008 | Recoules-Arche et al. | 606/99 |

(Continued)

OTHER PUBLICATIONS

Park et al., Comparison between Posterior and Transforaminal Approaches for Lumber Interbody Fusion. J Korean Neurosurg Soc 37, pp. 340-344, May 2005.

(Continued)

*Primary Examiner* — Christian Sevilla
(74) *Attorney, Agent, or Firm* — Alan W. Cannon; Law Office of Alan W. Cannon

(57) ABSTRACT

Implants, tools and methods for performing unilateral posterior lumbar interbody fusion are provided. An interbody implant includes a body having a top and bottom surface extending along a length thereof; and first and second side surfaces extending between the top and bottom surfaces on opposite sides of the body. The height of the first side surface is greater than the height of the second side surface.

12 Claims, 10 Drawing Sheets

(56) References Cited

U.S. PATENT DOCUMENTS

| | | |
|---|---|---|
| 2008/0177390 A1 | 7/2008 | Mitchell et al. |
| 2009/0216240 A1 | 8/2009 | Posdal |
| 2010/0152853 A1 * | 6/2010 | Kirschman ............... 623/17.11 |
| 2011/0301710 A1 | 12/2011 | Mather |

OTHER PUBLICATIONS

Shin et al., Posterior Lumber Interbody Fusion via a Unitateral Approach, pp. 1-10, Jun. 30, 2006.

* cited by examiner

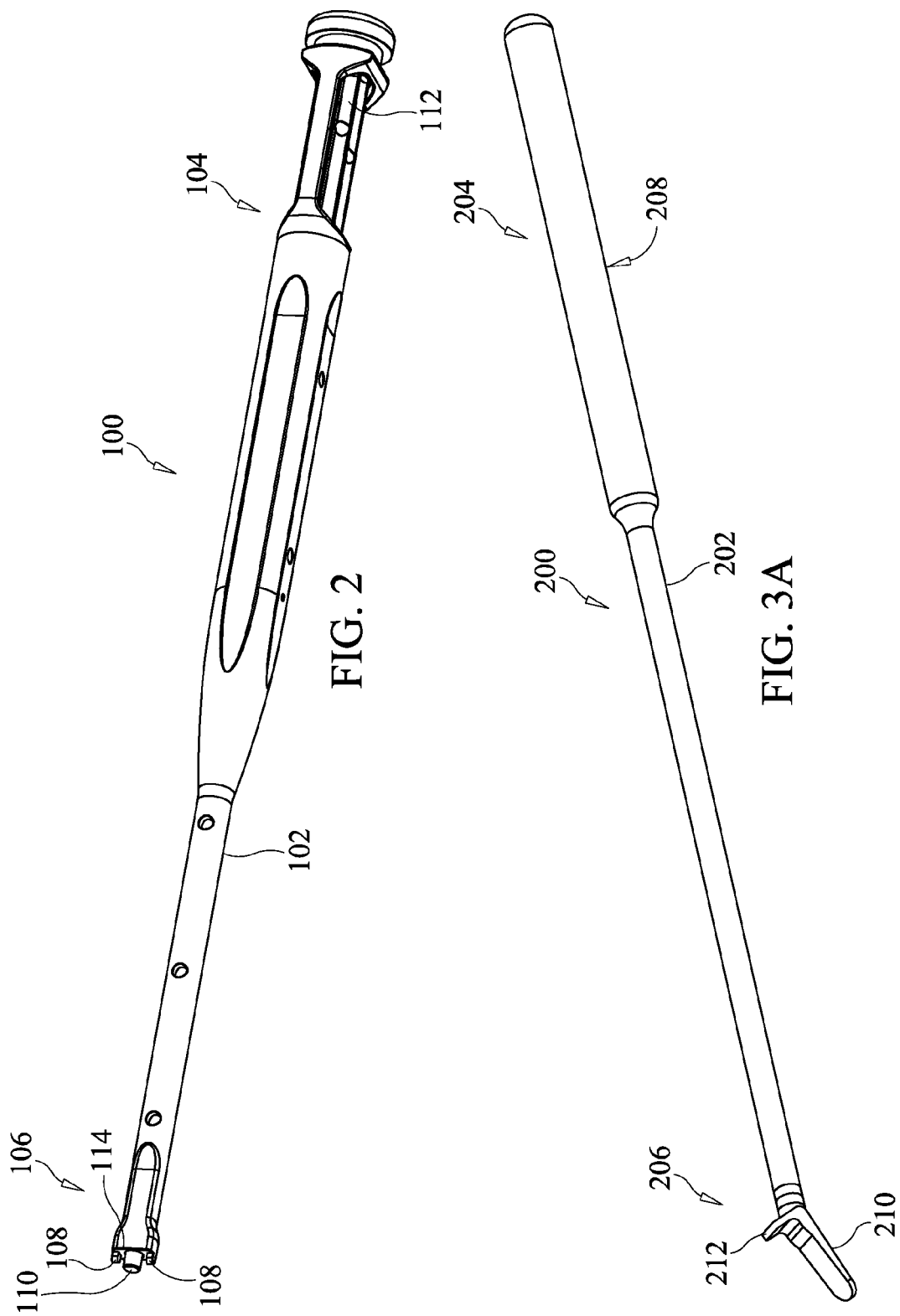

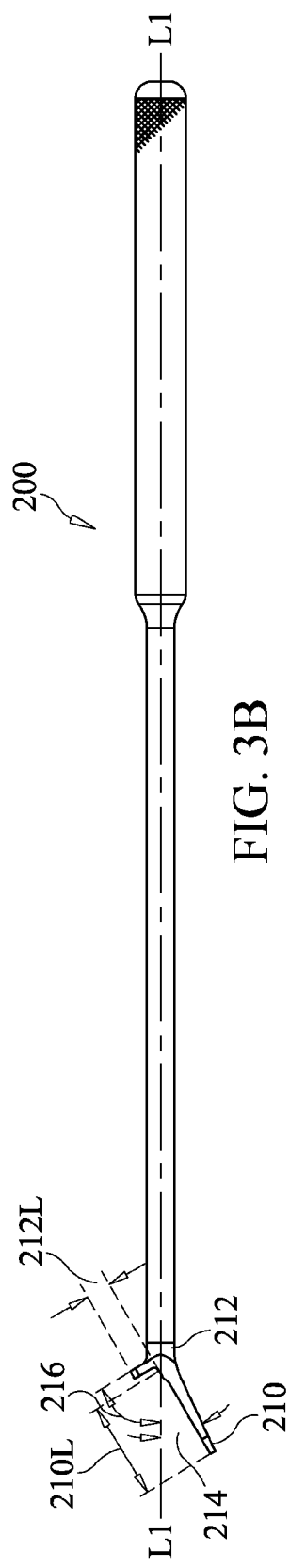
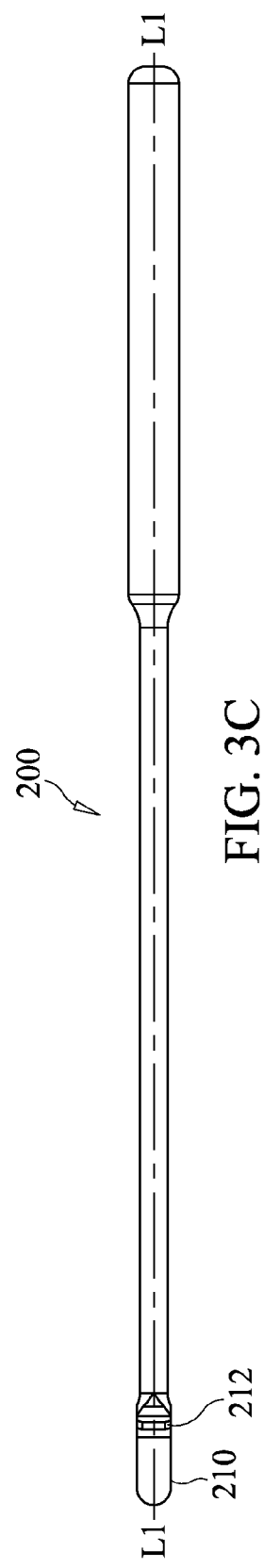
FIG. 3B
FIG. 3C

INTERVERTEBRAL IMPLANT FACILITATING UNILATERAL PLACEMENT, INSTRUMENTS AND METHODS

This application is a divisional application of copending application Ser. No. 12/792,040, filed Jun. 2, 2010, which is incorporated herein by reference in its entirety and to which application we claim priority under 35 USC §120.

BACKGROUND OF THE INVENTION

Back pain can be caused by a variety of factors, including, but not limited to the rupture or degeneration of one or more intervertebral discs due to degenerative disk disease, spondylolisthesis, deformative disorders, trauma, tumors and the like. In such causes, pain typically results from compression or irritation of spinal nerve roots by reduced spacing between adjacent vertebrae, a damaged disk and/or misalignment of the spine resulting of the injury or degeneration.

Common forms of treating such pain include various types of surgical procedures in which a damaged disk may be partially or totally excised, and one or more implants is inserted between adjacent vertebrae in an effort to restore the natural spacing and alignment between the vertebrae that existed previous to the injury or degeneration, so as to relieve the compression, irritation or pressure on the spinal nerve or nerves and thereby eliminate or significantly reduce the pain that the patient is experiencing. Typically, the one or more implants are used together with substances to encourage bone ingrowth to facilitate fusion between the adjacent vertebrae. Some procedures provide implants that allow at least some limited motion between the adjacent vertebrae, even after opposite ends of the implant are fixed to the adjacent vertebrae, respectively.

Among know procedures for performing fusion are PLIF (posterior lumbar interbody fusion), ALIF (anterior lumbar interbody fusion) and TLIF (transverse or transforaminal lumbar interbody fusion). A PLIF procedure achieves spinal fusion in the low back by inserting an implant such as a cage and, typically, graft material (to encourage bone ingrowth) directly into the disc space between adjacent vertebrae. The surgical approach for PLIF is from the back of the patient, posterior to the spinal column.

An ALIF procedure is similar to the PLIF procedure), except that in the ALIF procedure, the disc space is fused by approaching the spine through the abdomen, from an anterior approach, instead of through the lower back, from a posterior approach. Although previously there was a lot of interest in perfecting an endoscopic approach for ALIF surgery, it has largely been abandoned because it placed the great vessels (aorta and vena cava) at too great a risk.

A TLIF procedure involves a posterior and lateral approach to the disc space. To gain access to the disc space, the facet joint may be removed whereby access is gained via the nerve foramen. Typically only a single implant is placed in a TLIF procedure. The implant is inserted from a postero-lateral approach, as noted, and is ultimately placed in the middle-to-anterior aspect of the disc space.

There are certain conditions where a unilateral PLIF procedure is superior to a TLIF procedure. Such conditions include those where sever spinal stenosis is present. PLIF procedures typically place a pair of implants, one on each side of the disc space. To accomplish this, a typical approach forms two access ports into the disc space, both posterior to the spinal column, with one port one side relative to midline (the spinal process) and the other on the opposite side, relative to midline. Using this approach, each implant can be delivered and placed along a substantially direct delivery pathway. However, because two ports are formed, this results in a relatively large amount of removal of tissues, and risks nerve damage on both sides of the spinal column.

Alternatively, both implants may be delivered using a unilateral PLIF technique in which only one port is formed on one side of the midline, posterior spinal column. This significantly reduces the amount of tissues that need to be removed and reduces the number of nerves at risk of being damaged by the procedure by half. A unilateral PLIF procedure requires the first implant, after being inserted into the disc space, to be laterally driven over the midline of the intervertebral disc space and into position in the opposite side of the disc space. Drawbacks to current procedures include difficulties in laterally driving the first implant from one side of the disc space to the other. During this process, when using an implant/cage that has substantially equal heights on both sides of the implant/cage the leading side of the implant often resists moving in the transverse direction towards the opposite side of the disc space, and may dig into the annulus fibrosus and resist transverse driving of the implant. Moreover, the use of standard instruments such as cage inserters, end impactors, curved curettes, curved chisels, etc. often result in breaking the implant, when used to try to drive the implant from one side of the disc space to the other. This poses a serious risk of nerve root injury and/or injury to other body structures when an instrument breaks or a cage breaks, or during the process of removing a broken cage. Additionally, there are cases were a broken cage is unable to be completely removed and this compromises a successful fusion outcome.

The use of two implants in a PLIF procedure as opposed to the use of one implant, such as in a TLIF procedure, has been noted to markedly improve interbody fusion. However, it would be further advantageous to fusion resulting from a two implant procedure if the implants could be further laterally spaced from the midline of the intervertebral disc space, compared to current two implant procedures, as this would further enhance a honeycomb formation of fusion.

There is a continuing need for implants, instruments and procedures for performing unilateral PLIF to facilitate safer and easier delivery of the first implant form one side of the disc space to the opposite side. There is a continuing need to implants instruments and procedures designed to permit placement of the implants further laterally from the midline of the intervertebral space than is possible using current implants, tools and procedures. The present invention meets at least all of the above needs.

SUMMARY OF THE INVENTION

In one aspect of the present invention an interbody implant includes an implant body having a top and bottom surface extending along a length of the body and also defining a width of the body; and first and second side surfaces extending between the top and bottom surfaces on opposite sides of the body, the first side surface defining a first height and the second side surface defining a second height; wherein the first height is greater than the second height.

In at least one embodiment, the first height is greater than the second height by a difference in the range of about 1.8 mm to about 2.2 mm.

In at least one embodiment, an average height of the first side surface over a length from a distal end to a proximal end of the body is greater than an average height of the second side surface over the length from the distal end to the proximal end.

In at least one embodiment, the first height, measured at a particular location along the length of the body is greater than the second height, measured at the particular location along the length.

In at least one embodiment, the first height is greater than the second height at all corresponding locations along the length of the body.

In at least one embodiment, the body is substantially trapezoidal-shaped in a cross section taken normal to a longitudinal axis of the body.

In at least one embodiment, the top and bottom surfaces are radiused to join the second side surface having a lower height than the first side surface.

In at least one embodiment, the first and second side surfaces are substantially planar and flat.

In at least one embodiment, a series of retropulsion resistors are provided on the top and bottom surfaces, adjacent the first and second side surfaces, with each of the retropulsion resistors being configured to prevent retropulsion of the implant out of the interbody space.

In at least one embodiment, the retropulsion resistors comprise teeth configured to resist movement of the body out of the interbody space.

In at least one embodiment, at least portions of the top and bottom surfaces are convexly curved in a direction along a longitudinal axis of the body.

In another aspect of the present invention, an instrument for driving an interbody implant is provided that includes: a rigid elongated shaft having proximal and distal end portions; a handle formed at the proximal end portion; and a working end formed at a distal end of the instrument and extending from the distal end portion, the working end including a first member and a second member, the first member being longer than the second member, the first member forming a first angle with a longitudinal axis of the instrument and the second member forming a second angle with the longitudinal axis.

In at least one embodiment, the first member is a first foot and the second member is a second foot, the first and second angles opening toward a distal direction, and the first angle being smaller than the second angle.

In at least one embodiment, the first member and the second member form substantially a right angle therebetween.

In at least one embodiment, the first angle is in the range of about twenty degrees to forty degrees and the second angle is in the range of about fifty degrees to about seventy degrees.

In at least one embodiment, the first angle is about thirty degrees and the second angle is about sixty degrees.

In at least one embodiment, the first member is a foot and the second member is a knob configured to be received through a side opening of the interbody implant, the first and second angles opening toward a distal direction.

In at least one embodiment, the first angle is in the range of about thirty degrees to about sixty degrees and the second angle is in the range of about thirty degrees to about fifty degrees.

In at least one embodiment, the first angle is about forty degrees and the second angle is about fifty degrees.

In another aspect of the present invention, an interbody implant system is provided that includes: an interbody implant including an implant body having a top and bottom surface extending along a length of the body and also defining a width of the body; and first and second side surfaces extending between the top and bottom surfaces on opposite sides of the body, the first side surface defining a first height and the second side surface defining a second height; wherein the first height is greater than the second height; and an instrument for driving the interbody implant, the instrument including: a rigid elongated shaft having proximal and distal end portions; a handle formed at the proximal end portion; and a working end formed at a distal end of the instrument and extending from the distal end portion, the working end including a first member and a second member, the first member being longer than the second member, the first member forming a first angle with a longitudinal axis of the instrument and the second member forming a second angle with the longitudinal axis.

In at least one embodiment, the system includes a pair of the interbody implants.

In at least one embodiment, the instrument is a first instrument, the first member is a first foot and the second member is a second foot, the first and second angles opening toward a distal direction, and the first angle being smaller than the second angle; the system further comprises a second instrument, the second instrument including a second rigid elongated shaft having proximal and distal end portions; a second handle formed at the proximal end portion of the second shaft; and a second working end formed at a distal end of the second instrument and extending from the distal end portion of the second shaft, the second working end including a foot member and a knob, the foot member being longer than the knob, the foot member forming a third angle with a longitudinal axis of the second instrument and the knob forming a fourth angle with the longitudinal axis of the second instrument.

In another aspect of the present invention, a unilateral method of inserting first and second interbody implants is provided, the method including: creating an interbody port on one side of the spinal column, while maintaining structures of the spinal column and the lumbar musculoligamentous complex on an opposite side of the spinal column relative to the port, intact; removing disc material through an incision in an annulus fibrosus of a disc in communication with the port and through the port; inserting the first interbody implant through the port and into the disc space, wherein the first interbody implant has a first distal end portion, a first proximal end portion and first and second sides extending between the first distal end portion and the first proximal end portion, wherein a height of the first interbody implant on the first side is less than a height of the interbody implant on the second side, and wherein the first interbody implant is inserted such that the first side is medially placed and the second side is laterally placed on a first side of the disc space; driving the first interbody implant from a location in the disc space on the first side, over the median of the disc space and into a position in the disc space on a second side of the disc space, such that, as a result, the first side is laterally placed and the second side is medially placed on the second side of the disc; and inserting the second interbody implant through the port and into the disc space on the first side of the disc space, wherein the second interbody implant has a second distal end portion, a second proximal end portion and third and fourth sides extending between the second distal end portion and the second proximal end portion, wherein a height of the second interbody implant on the third side is less than a height of the second interbody implant on the fourth side, and wherein the second interbody implant is inserted such that the fourth side is medially placed and the third side is laterally placed on a first side of the disc space.

In at least one embodiment, the first and second interbody implants are each substantially trapezoidal-shaped in a cross section taken normal to a longitudinal axis thereof.

In at least one embodiment, the method includes distracting the disc space prior to the inserting steps, by applying distraction forces to vertebrae adjacent the disc space.

In at least one embodiment, the method includes packing each interbody implant, prior to the inserting, with a material that encourages bone ingrowth.

In at least one embodiment, the method further includes packing a space between the interbody implants, after insertion thereof, to encourage a honeycomb pattern of bone ingrowth into the disc space.

These and other advantages and features of the invention will become apparent to those persons skilled in the art upon reading the details of the implants, systems, instruments and methods as more fully described below.

BRIEF DESCRIPTION OF THE DRAWINGS

FIG. 2 is a perspective view of an embodiment of an inserter instrument used for the initial insertion of an implant according to the present invention.

FIG. 3A is a perspective view of a first side impactor instrument according to one embodiment of the present invention.

FIG. 3B is a plan view of the instrument of FIG. 3A.

FIG. 3C is another plan view of the instrument of FIG. 3A, with the instrument having been rotated ninety degrees about its longitudinal axis, relative to the plan view shown in FIG. 3B.

DETAILED DESCRIPTION OF THE INVENTION

Figure 1A:
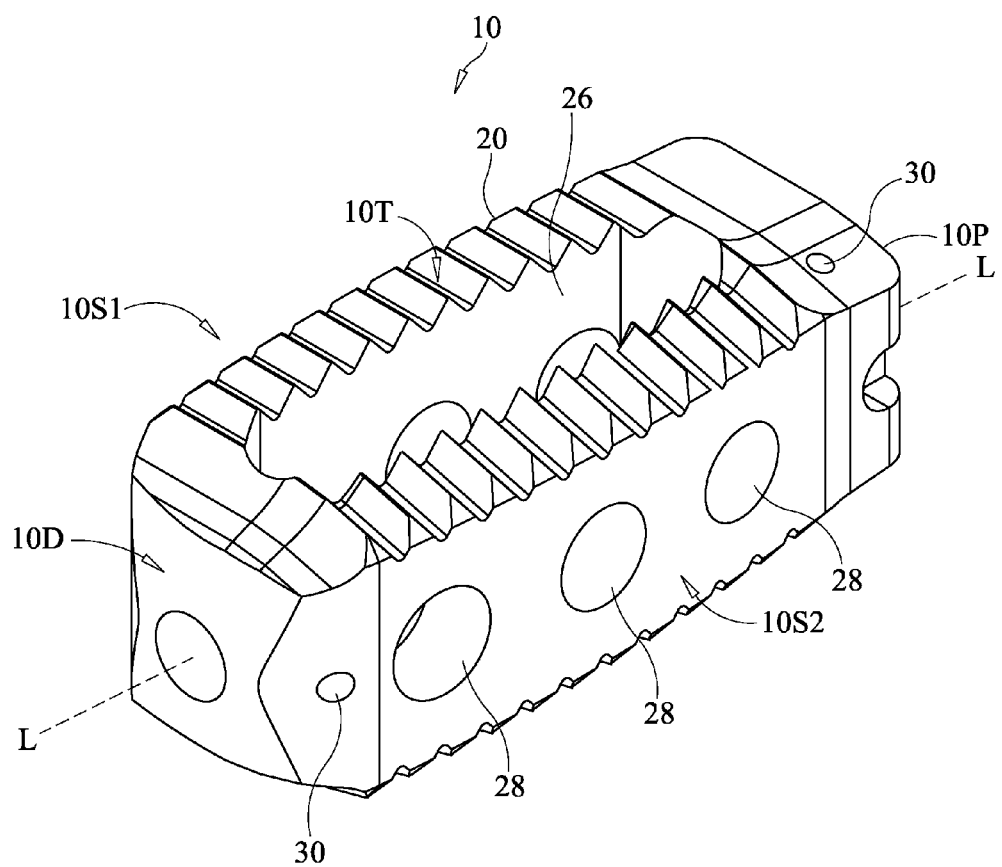
FIG. 1A is a perspective view of an implant according to an embodiment of the present invention.

Before the present implants, instruments and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an implant includes a plurality of such implants and reference to "the nerve" includes reference to one or more nerves and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "retropulsion resistor" is a feature configured to resist backing out of the implant once it has been finally placed, as well as at any location along its delivery pathway. One or more repulsion resistors may be formed in or on an implant, preferably in or on both top and bottom surfaces of the implant.

A "tooth" as defined herein, refers to a feature having a peak such as an edge designed to function as a retropulsion resistor. For example a series of teeth may be provided to form a sawtooth-like pattern so as to resist retropulsion. In a preferred embodiment, the sides of the teeth are symmetrical. Alternatively, the sides may be asymmetrical, forming a "shark-tooth pattern", wherein the apex of the tooth is biased either toward the distal end portion of the implant or proximal end portion of the implant, preferably toward the distal end portion.

"Honeycomb grafting" refers to a technique in which graft material (e.g. autograft or allograft cancellous bone) is laid down in a graft site to form a network of interstice containing hematipoietic elements, wherein the interstices are arranged in a honeycomb like network formation. The honeycombed network enhances the osteoinductive, osteogenic and osteoconductive properties of the bone grafted as well as the chance of obtaining a fully integrated region of new bone.

Figure 1B:
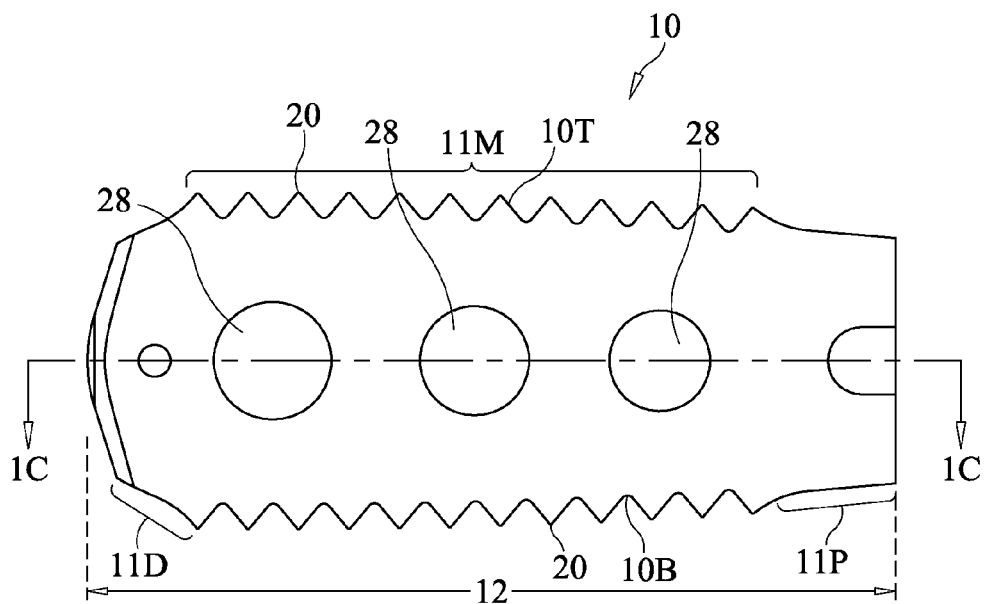
FIG. 1B is a side view of the implant of FIG. 1A.
Figure 1C:
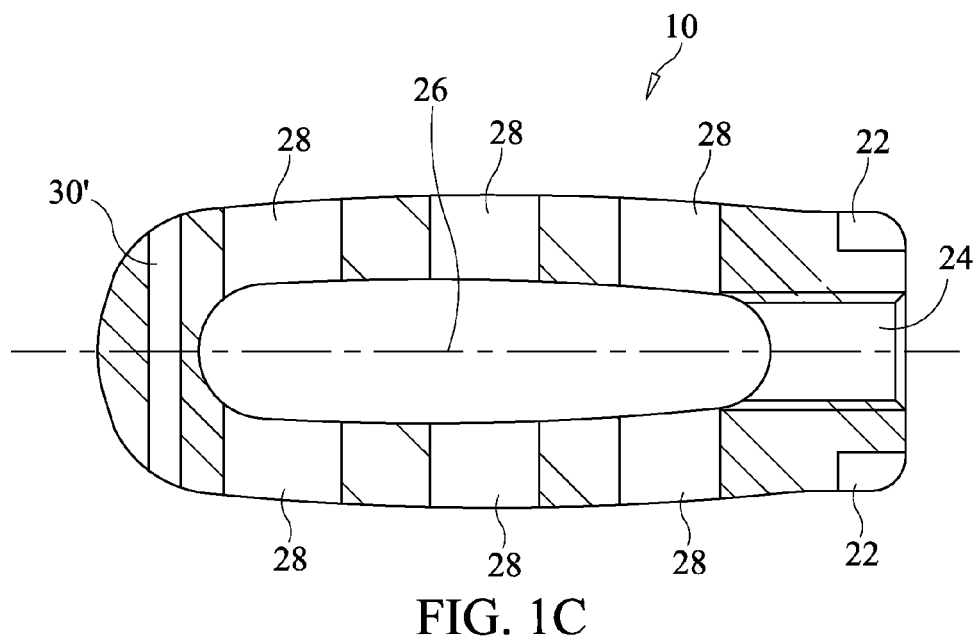
FIG. 1C is a longitudinal sectional view of the implant of FIG. 1B taken along line 1C-1C.
Figure 1D:
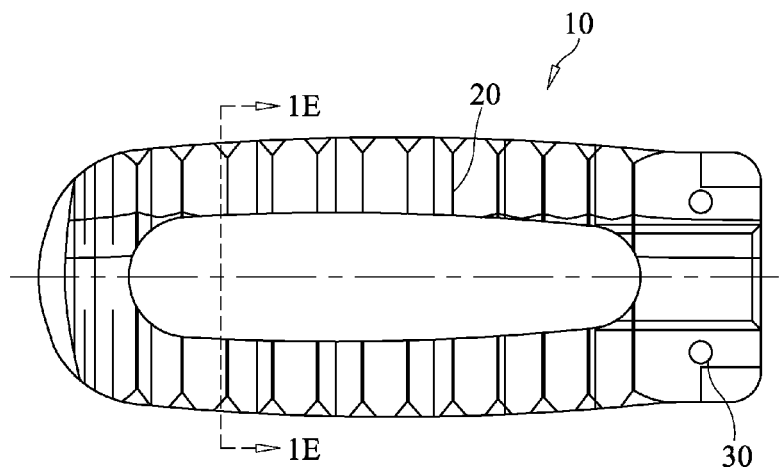
FIG. 1D is a top view of the implant of FIG. 1A.

Referring now to the drawings in detail, FIGS. 1A-1B show a perspective view and a side view, respectively, of an implant 10 according to an embodiment of the present invention. FIG. 1C is a longitudinal sectional view of FIG. 1B taken along line 1C-1C. FIG. 1D is a top view of the implant 10 of FIG. 1A and FIG. 1E is a cross sectional view of FIG. 1D taken along line 1E-1E.

Implant 10 is formed of a unitary body having a length 12 (see FIG. 1B), width dimension 14 (see FIG. 1E) and height dimension 16 (see FIG. 1E). 1. The body includes a top surface 10T and a bottom surface 10B extending along the length 12 of the implant 10 and also defining the width of the implant body. The top and bottom surfaces 10B, 10T may be mirror images of one another, as illustrated in FIG. 1B.

First and second side surfaces 10S1 and 10S2 extend between the top 10T and bottom 10B surfaces on opposite sides of the implant 10 body. The first side surface 10S1 defines a first height 16S1 and the second side surface 10S2 defines a second height 16S2. The first height 16S1 is greater than the second height 16S2 by a predefined amount.

Figures 1E, 1F:
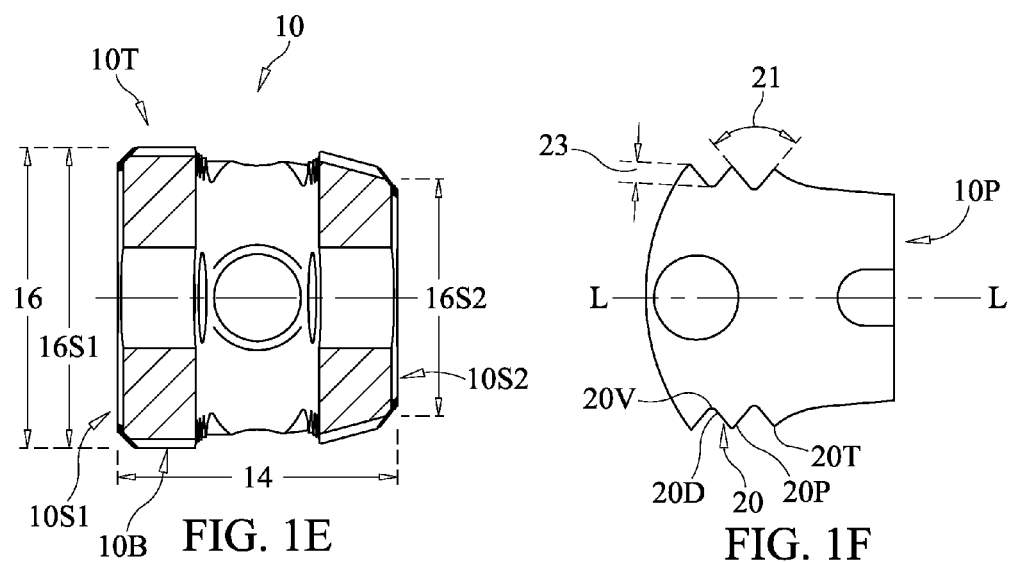
FIG. 1E is a cross-sectional view of the implant of FIG. 1D taken along line 1E-1E.
FIG. 1F is a detail view of the portion of FIG. 1B captured by circle 1F.

In the embodiment of FIG. 1E, the implant body is radiused or otherwise tapered in a direction extending from the midline along the longitudinal axis L-L thereof toward the second side surface 10S2. Thus, top and bottom surfaces 10T and 10B are tapered or beveled as illustrated in FIG. 1E, starting from a height (separation distance of top and bottom surfaces) of 16S1, down to a height (separation between top and bottom surfaces) of 16S2, as shown in FIG. 1E. The embodiment of FIGS. 1A-1E in this way provides a body that is substantially trapezoidal-shaped in a cross section taken normal to a longitudinal axis of the body, as illustrated in FIG. 1E. Variations of the cross-section shown in FIG. 1E include those in which the shape of the top 10T and/or bottom 10B surfaces are curved or straight. When straight, they may have the same or different inclinations. When curved, they may have the same or different radii of curvature.

In general, by providing an implant body that has a first side 10S1 that has a height 16S1 that is substantially greater than a height 16S2, of an opposite side (second side) 10S2, whether the cross-section shape is trapezoidal or some other shape, the tapered shape of the implant top and bottom surfaces 10T, 10B joining the second side 10S2 facilitates driving the implant 10 laterally with the side 10S2 having reduced height 16S2 being the leading side of the implant during lateral driving. This helps prevent snagging, catching or digging in of the implant side 10S2. This also allows the implant to be driven further laterally than what is possible when using an implant that has a substantially square or substantially rectangular cross-section, where both sides have the same height, because of the biconcave shape of the disc space. The ability to place the implants further laterally relative to the midline of the disc space allows relatively more bone graft to be placed in between (medial of) the two implants, which greatly enhances the ability to achieve a desired "honeycomb" pattern of grafting, resulting in the achievement of a superior fusion. Additionally, by providing an implant body that has a first side 10S1 that has a height 16S1 that is substantially greater than a height 16S2, of an opposite side (second side) 10S2, this reduces the amount of lateral force that needs to be applied to the implant to drive it laterally from one side of the disc space to the other, relative to the amount of force that is needed to drive an implant having first and second sides of substantially equally height. Accordingly, this design of the implant reduces the risk of breaking the implant 10 during lateral driving, as relatively less lateral force needs to be applied to drive the implant 10 laterally as described.

In at least one embodiment, the height 16S1 is greater than the second height 16S2 by a difference in the range of about 1.8 mm to about 2.2 mm. In at least one embodiment, the average height of the first side surface 10S1 over a length from a distal end to a proximal end of the implant 10 body is greater than the average height of the second side surface 10S2 over the length from the distal end 10D to the proximal end 10P. Preferably the first height 16S1, measured at any particular location along the length 12 of the first side 10S1 is greater than the height 16S2 of the second side 10S2, measured at the same location along the length 12 on the second side 10S2. Preferably, each height difference between 16S1 and 16S2 at a same corresponding location along length 12 is in the range of about 1.8 mm to about 2.2 mm, typically about 2 mm. Thus, the first height 16S1 is preferably greater than the second height 16S2 at all corresponding locations along the length of the implant body.

Implant 10 is a substantially straight implant. Thus, side surfaces 10S1 and 10S2 are preferably substantially aligned with the longitudinal axis L-L of the implant 10, and are substantially planar and flat. The exception to this are the locations along the distal end portion 11D and the proximal end portion 11P where the side surfaces 10S1 and 10S2 taper toward one another to defined the reduced widths of the proximal and distal end portions 11P,11D, relative to the main body portion 11M.

A series of retropulsion resistors, such as teeth 20 may be formed on the top 10T and bottom 10B surfaces, adjacent the first and second side surfaces, as shown in FIGS. 1A-1B, for example. The retropulsion resistors 20 are configured to prevent retropulsion of the implant 10 out of the interbody space once it has been implanted there. The top and bottom surfaces 10T, 10B may be convexly curved in a direction along the longitudinal axis L-L of the implant, which may better conform the top and bottom surfaces to the vertebrae forming the interbody disc space, as the vertebrae surfaces forming the interbody disc space are concave in the anterior-posterior direction, as well as the latero-medial direction. The convexity of the top and bottom surfaces 10T, 10B also results in reduced height of the distal and proximal portions 11D, 11P relative to the height of the central portion 11M on the same side of the implant 10. This condition is true for both sides 10S1, 10S2. The reduced height of the distal end 10D and the tapered, varying height of the distal end portion 11D facilitate insertion of the implant 10 between adjacent vertebral bodies. The reduced height of the proximal end 10P and tapered, varying height of the proximal end portion 11P better conform this portion to the shape/contours of the inter-vertebral disk space for improved load sharing, that is with a more even load distribution over the length of the implant 10. Implants 10 can be manufactured to have a variety of sizes to accommodate different sizes of patients and different inter-vertebral locations. In one non-limiting example, implants 10 may be manufactured in lengths 12 of 22 mm, 24 mm, and 26 mm and in 1 mm height 16S1 increments from 7 min to 15 min (each having the requisite height differential between height 16S1 and height 16S2). The width 14 may be about 9 mm or about 10 min or in the range of about 9 mm to about 10 mm, although this may also vary.

The proximal end 10P of implant 10 includes a pair of slots 22 and a threaded bore 24 which facilitates positive engagement of an inserter instrument 100 in a manner described in more detail below.

Implant 10 is formed as a cage having a unitary body, with openings provided through the top and bottom surfaces 10T, 10B to form cavity 26, wherein the opening formed in the top surface 10T is in communication with the opening formed in the bottom surface 10B and is configured and dimensioned to receive graft material, such as bone particles or chips, demineralized bone matrix (DBM), paste, bone morphogenetic protein (BMP) substrates or any other bone graft expanders, or other substances designed to encourage bone ingrowth into the cavity 26 to facilitate the fusion. Although shown as a single, large cavity 26, implant 10 may be alternatively configured to provide two or more cavities that extend from top to bottom of the implant body 10 and through top and bottom surfaces 10T, 10B and provide the same function as cavity 26.

Additionally implant 10 is provided with one or more side openings 28 as shown in FIGS. 1A-1C. In the embodiment shown, three side openings 28 are provide through both sides 10S1, 10S2 and are aligned with one another, as shown in FIG. 1C. Side openings 28 facilitate retention of the graft material in a honeycomb-like configuration and also encourage ingrowth or bone to form a honeycomb like capture of the implant 10. Additionally, at least one side opening 28 may function as an interface with a side impactor tool during lateral driving of the implant 10, as described in more detail below.

Implant 10 is preferably made from PEEK (polyetheretherketone) and is preferably machined therefrom, but alternatively, may be manufactured by injection molding or three-dimensional lithographic printing, for example. When manufactured by three-dimensional lithographic printing, implant 10 may be made of polymers, such as PEEK or other polymer and/or absorbable materials such as tri-calcium phosphate (TCP), hydroxyapatite (HA) or the like. When made of metal (titanium, stainless steel or other biocompatible metal or metal alloy, implant 10 may be machined or made by metal powder deposition, for example. Alternatively, implant 10 may be made of PEKK (poly(oxy-p-phenyleneisophthaloyl-phenylene/oxy-p-phenyleneterephthaloyl-p-phenylene) or carbon-filled PEEK. Manufacturing the implant from any of these polymer materials makes it radiolucent, so that radiographic visualization can be used to view through the implant 10 to track the post-procedural results and progress of the fusion over time. Alternatively, implant 10 could be made of titanium or other biocompatible, radiopaque metal. However, this is less preferred as this type of implant would obscure post-procedural radiographic monitoring.

In order to facilitate visualization of the implant 10 during the procedure, so as to confirm that the implant is being delivered along a desirable delivery pathway and that the implant 10 is maintaining a desirable orientation, implant 10 is provided with at least three radiopaque markers 30. In the example shown, one marker 30 is provided adjacent side 10S1 at or near the top surface 10T of the proximal end portion (FIG. 1A), a second marker 30 is provided adjacent side 10S2 at or near the bottom surface 10B of the proximal end portion (illustrated in phantom in FIG. 1D), and a third marker 30 is provided horizontally, adjacent the distal end portion (See FIG. 1A) in a location 30' (FIG. 1C) between sides 10S1 and 10S2. By placing radiopaque markers 30 as described, this enables radiographic viewing of the markers 30, at any location along the delivery pathway and during the procedure, as well as post-procedurally, to accurately determine the three-dimensional positioning of the implant 10. Thus, not only can the radiographic imaging determine the location that the implant 10 is placed in, it can also determine the three-dimensional orientation of the implant relative to the anatomy at the location that it is placed in.

As shown, retropulsion resistors are provided on both top and bottom surfaces 10T, 10B along two longitudinally extending locations, as a plurality of teeth that extend adjacent sides 10S1 and 10S2. Each tooth 20 angles outwardly over a direction from a most inset portion (referred to as a valley) 20V toward tip or peak 20T, as illustrated in FIG. 1F. Tooth 20 is symmetrical, such that distal side 20D of tooth 20 is of equal length to proximal side 20P, and a line drawn through the peak 20t perpendicular to the top 10T or bottom 10B surface bisects the angle formed by the sides 20D and 20P. Alternatively, teeth 20 may be biased toward the distal end (or proximal end, but preferably toward the distal end) of the implant 10, such that the distal side 20D of tooth 20 is shorter (or longer) than the proximal side 20P of tooth 20. The angle 21 formed by a proximal side 20P and a distal side 20D extending from valley 20V is about forty-five to about ninety degrees. In the embodiment shown in FIG. 1F, angle 21 is about eighty degrees. The height 23 of tooth 20 measured in a direction perpendicular to the longitudinal axis L-L/top surface 10T/bottom surface 10B is about 0.5 mm to about 1.0 mm. In the embodiment shown in FIG. 1F, height 23 is about 0.75 mm. Thus, the height of peak 201 above valley 20V in FIG. 1F is about 0.75 mm, measure in the height direction perpendicular to the longitudinal axis L-L.

Once implant 10 has been inserted and placed as desired in the disc space, and distraction is removed, teeth 20 resist movement of the implant 10 toward the proximal direction, as the peaks 20T of the teeth 20 bite into the bone/tissue and acts as an anchor or brake that prevents the backing out or substantial proximal movement of the implant 10.

Figure 5A:
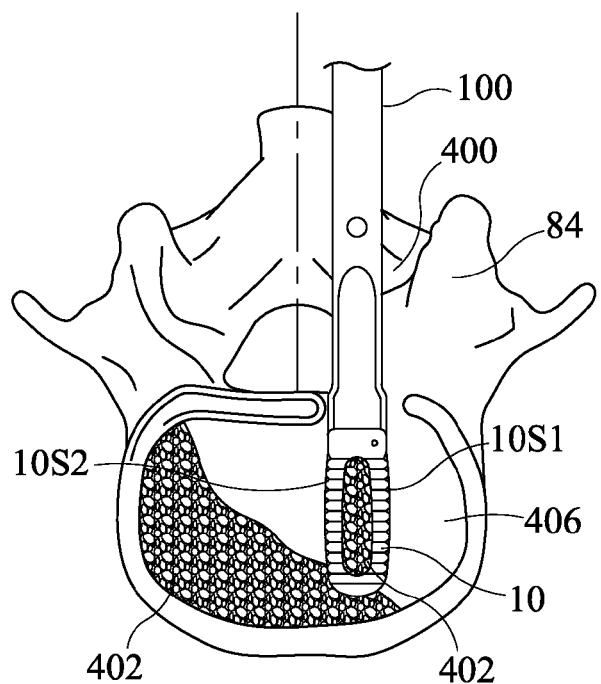
FIGS. 5A-5F illustrate a method of inserting a pair of implants using a unilateral PLIF method according to an embodiment of the present invention.

FIG. 2 shows a perspective view of an inserter instrument 100 configured and dimensioned for inserting implant 10 between adjacent vertebral bodies. Insertion instrument 100 is a straight instrument, having a substantially straight, elongate shaft 102 having a proximal end portion 104 and a distal end portion 106. The distal end portion 106 includes the working, end of the instrument that includes a pair of posts 108, one on either side of threaded shall 110. An actuation knob 112 is provided at the proximal end portion of instrument 100. Actuation knob 112 is rotatable relative to shaft 102, but rotatably fixed relative to threaded shaft 110. Actuation knob is rotatable around the axis of the inserter and the central shaft rotates along with it. By aligning the posts 108 with slots 22 and aligning threaded shaft 110 with threaded bore 24, actuator knob 112 can be rotated relative to shaft 102 to screw the threaded shaft 110 into the threaded bore 24. This causes the working end of instrument 100 to be drawn up against the proximal end 10P of implant 10, including drawings the posts 108 into slots 22 such that the contact surface 114 of the working end abuts against the proximal end 10P of the implant as shown in FIG. 5A, with implant 10 having been securely joined to instrument 100, such that implant 10 can neither translate nor rotate relative to instrument 100. To release the implant 10, the actuation knob 112 is simply reverse-rotated until threaded shaft 110 separates from threaded bore 24, after which instrument 100 can be withdrawn without affecting the positioning of implant 10.

FIG. 3A is a perspective view of a first side impactor instrument 200 according to an embodiment of the present invention. First side impactor instrument 200 has a substantially straight, rigid, elongate shaft 202 having a proximal end portion 204 and a distal end portion 206. Whereas insertion instrument 100 is configured and dimensioned to insert the implant 10 into the disc space along a substantially straight delivery pathway in a posterior to anterior direction, first side impactor 200 is configured to drive the implant in a lateral-medial direction from one side of the disc space toward the other side, after the insertion instrument 100 has been used to initially place the implant 10 on a first side of the disc space, which is the side aligned with the port through which the implant 10 is introduced into the disc space. A handle 208 is formed at the proximal end portion 204 of instrument 200. Handle 208 hits an outside diameter that is greater than the outside diameter of shaft 202 distal to handle 208. The enlarged diameter of handle 208 facilitates the manipulation of the instrument 200 by the surgeon for use in laterally driving implant 10.

The distal end portion 206 includes a working end that includes first and second working members 210, 212. First working member 210 is longer that second working member 212. First working member 210 has a length 210L in the range of about eighteen mm to about twenty-two mm. In the embodiment shown in FIGS. 3A-3C, first working member 210 has a length 210L of about twenty mm. Second working member 212 has a length 212L in the range of about three mm to about seven mm. In the embodiment shown in FIGS. 3A-3C, second working member 212 has a length 212L of about four mm.

First working member 210 forms an angle 214 with the longitudinal axis L1-L1 of instrument 200, angle 214 opening toward the distal direction, that is in the range of about twenty degrees to about forty degrees. In the embodiment shown in FIG. 3B, angle 214 is about thirty degrees. Second working member 212 forms an angle 216 with the longitudinal axis L1-L1 of instrument 200, angle 216 opening toward the distal direction, that is in the range of about fifty degrees to about seventy degrees. In the embodiment shown in FIG. 3B, angle 214 is about sixty degrees. Thus, the angle formed between first and second working members foot 210 and foot 212) and that opens to the distal direction is a about ninety degrees. First and second members 210, 212 of instrument 200 are also referred to as "feet" and are substantially flat plates that are configured to substantially conform to and engage the proximal end 10P (working member 212) and side 10S1 (the taller side is engaged by working member 210) of implant 10, respectively. FIG. 3C is another plan view of instrument 200 with the instrument 200 having been rotated by ninety degrees about longitudinal axis L1-L1, relative to the orientation shown in FIG. 3B. Working members 210 and 212 are substantially aligned with in the plane in which the longitudinal axis L1-L1 extends in the view shown in FIG. 3C.

Figures 4A, 4B:
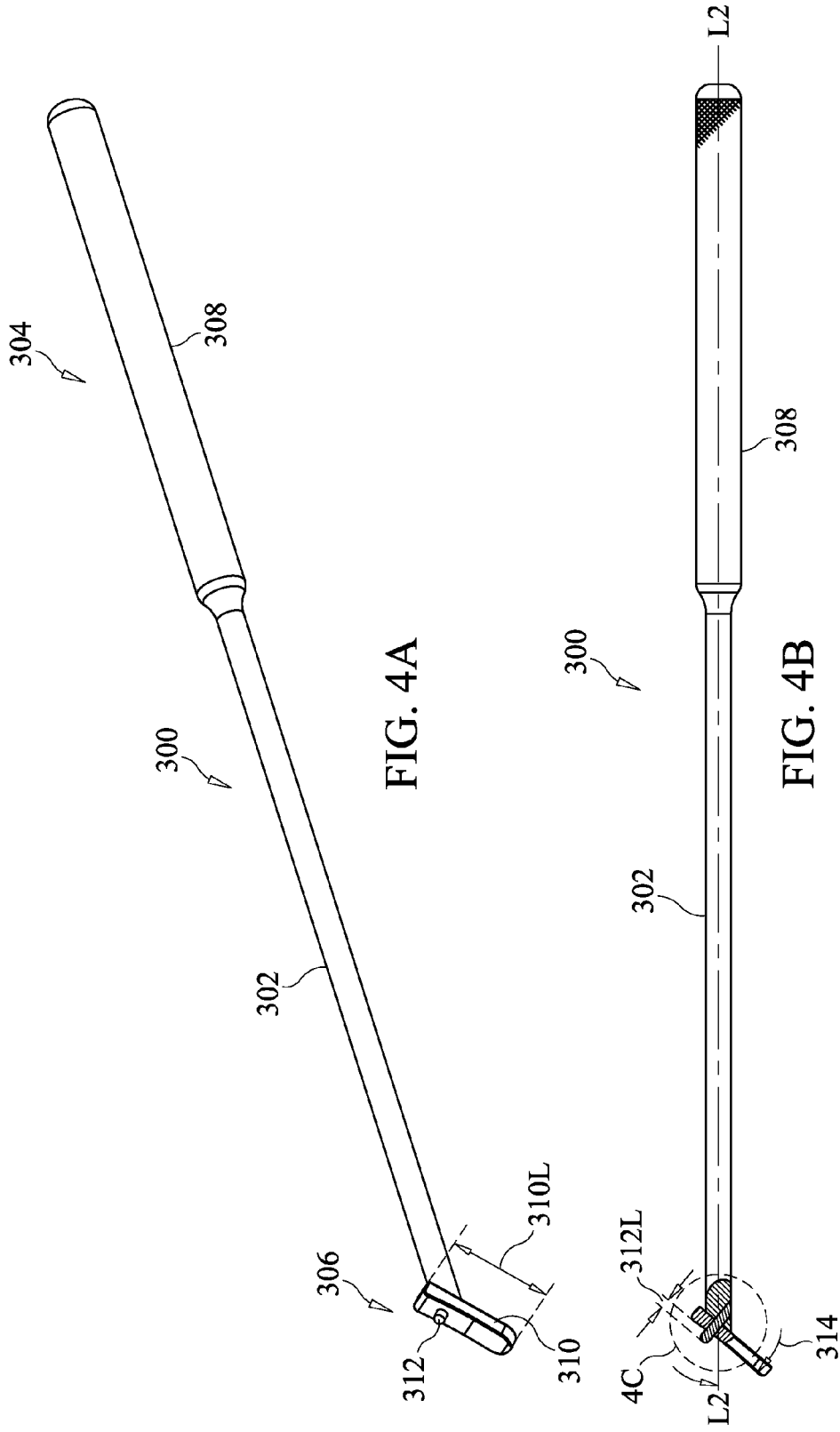
FIG. 4A is a perspective view of a second side impactor instrument according to one embodiment of the present invention.
FIG. 4B is a plan view of the instrument of FIG. 4A.

FIG. 4A is a perspective view of a second side impactor instrument 300 according to an embodiment of the present invention. Second side impactor instrument 300 has a substantially straight, rigid, elongate shaft 302 having a proximal end portion 304 and a distal end portion 306. Second side impactor 300 is configured and dimensioned to drive implant 10 further across the disc space in the lateral-medial (or medial to lateral direction, if the implant has crossed the median of the disc space) so as to position it in the opposite side of the disc space. Second side impactor instrument 300 is configured for use in driving the implant 10 after the first side impactor 200 has been used to drive the implant partially across the disc space, transverse to the posterior-anterior direction. A handle 308 is formed at the proximal end portion 304 of instrument 300. Handle 308 has an outside diameter that is greater than the outside diameter of shaft 302 distal to handle 308. The enlarged diameter of handle 308 facilitates the manipulation of the instrument 300 by the surgeon for use in driving implant 10 transversely.

The distal end portion 306 includes a working end that includes first and second working members 310, 312. First working member 310 is longer that second working member 312. First working member 310 has a length 310L in the range of about sixteen mm to about twenty-two mm. In the embodiment shown in FIGS. 4A-4D, first working member 310 has a length 310L of about eighteen mm. Second working member 312 has a working length 312L extending from the surface of working member 310 in the range of about 1.5 mm to about 3.5 mm. In the embodiment shown in FIGS. 4-4D, second working member 312 has a working length 312L of about 2.5 mm.

First working member 310 forms an angle 314 with the longitudinal axis L2-L2 of instrument 300, angle 314 opening toward the distal direction, that is in the range of about thirty degrees to about sixty degrees. In the embodiment shown in FIG. 4B, angle 314 is about fifty degrees. Second working member 312 forms an angle 316 with the longitudinal axis L2-L2 of instrument 300, angle 316 opening toward the distal direction, that is in the range of about thirty degrees to about fifty degrees. In the embodiment shown in FIGS. 3B-3C, angle 314 is about forty degrees. Thus, the angle formed between first and second working members (foot 310 and knob 312) and that opens to the distal direction is a about ninety degrees. First member 310 of instrument 300 is also referred to as foot 310. Foot 310 is a substantially flat plate except for the location that member 312 extends out from. Second member 312 is also referred to a knob 312. Knob 312 is substantially cylindrical in the embodiment shown, and is configured to be inserted into and engage with one of openings 28 in implant 10, typically, the proximal most opening 28. It should be noted here that although opening 28 and knob 312 are substantially circular in cross-section, that the present invention is not limited to this configuration, as these inter-engaging components could be made to have any of a number of various other shapes in cross-section, including, but not limited to oval, square, triangular, irregular, hexagonal, or the like. The working end of instrument 300 is configured to substantially conform to and engage the side 10S1 (the taller side) of implant 10 for applying lateral force thereto. Thus, knob 312 is inserted into opening 28 and the surface of foot 310 substantially conforms to and engages the surface of side 10S1.

Figure 4C:
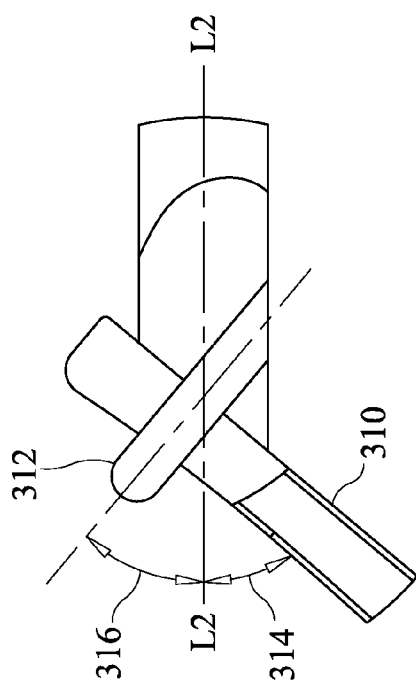
FIG. 4C is an enlarged view of the portion of the instrument shown in FIG. 4B within circle 4C.
Figure 4D:
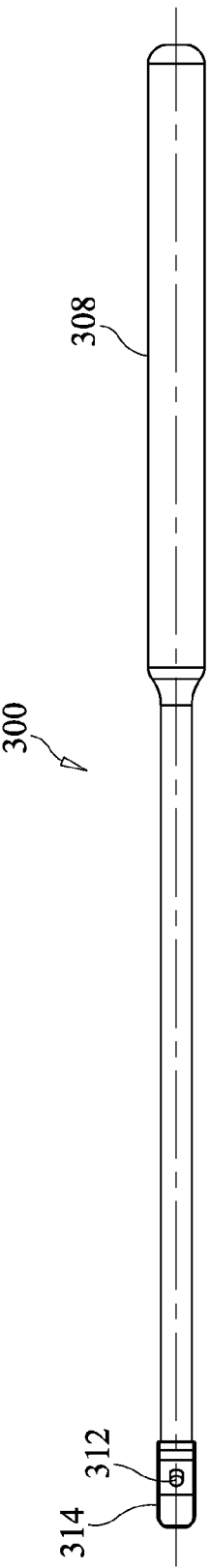
FIG. 4D is another plan view of the instrument of FIG. 4A, with the instrument having been rotated ninety degrees about its longitudinal axis, relative to the plan view shown in FIG. 4B.

FIG. 4C is an enlarged, detail view of the working end that better shows the configuration of the foot 310 and knob 312, and the angles that they are oriented at relative to the longitudinal axis L2-L2, as well as the substantially right angle that they form relative to one another. FIG. 4D is another plan view of instrument 300 with the instrument 300 having been rotated by ninety degrees about longitudinal axis L2-L2, relative to the orientation shown in FIG. 4B. Working members 310 and 312 are substantially aligned in the plane in which the longitudinal axis L2-L2 extends in the view shown in FIG. 4D.

FIGS. 5A-5E illustrate a method of inserting a pair of implants using a unilateral PLIF method according to an embodiment of the present invention. This method is performed with the patient in a position of natural lordosis, either in the prone position or in a "relaxed" knee-chest position. A skin incision is made posterior to the spine and lateral to the medial line for preparation of the insertion port 400. Once the insertion port 400 has been established (which can be established using known techniques), the disc material is removed with an instrument such as a bone curette, by insertion of the curette through the port (the window into the foramen), and an incision in the annulus fibrosus. At least the anterior and lateral walls of the annulus fibrosus are preferably preserved as much as possible to provide additional support for the implants 10.

The cartilaginous layers on the surfaces of the vertebral endplates are removed, using an instrument such as a bone rasp, until bleeding is attained. Sufficient cleaning of the endplates is decisive for vascular supply of the bone graft. However, excessive cleaning risks damaging the denser bone layer and weakening the endplate, so care should be taken not to excessively remove the cartilaginous tissues.

Next, a first implant 10 is prepared for insertion. First implant 10 is fixed to inserter instrument 100 by operating actuation knob 112 to screw threaded shaft 110 into threaded bore 24 and drawing posts 108 into slots 22 in a manner described above. The hollow spaces defined by openings 26, 28 are then filled with graft material 402. In one particular embodiment, graft material 402 is autologous bone harvested, for example, from the iliac crest of the patient. However, any of the other alternative materials described above could be substituted for use as graft material 402 to fill the cavities in the implant 10. The second implant 10 can likewise be filled at this time (before or after attachment to a second inserter instrument 100. Additionally, graft material can be filled into the anterior portion of the disc space 406 and a portion of the side of the disc space opposite of the side into which the port 400 enters, prior to insertion of the first implant 10. The vertebrae adjacent (superior and inferior to, respectively) to the disc space 406 are distracted to provide additional working space therebetween, and allow a temporary increase in the disc space 406.

After preparation as described above, the first implant 10 is inserted, using inserter instrument 100 as illustrated in FIG. 5A. Prior to insertion, it must be confirmed that the side 10S2 having relatively less height is oriented so that it is facing the disc space. This orientation is required to facilitate transverse driving of the implant 10, as during such driving, the shorter, tapered side 10S2 reduces the friction generated, compared to a symmetrical cage where such leading side is not tapered and is of equal height to the trailing side. Also, since the side 10S2 is tapered at both top and bottom where it joins the top 10T and bottom 10B surfaces, this greatly reduces the risk that the side 10S2 will catch or snag on tissue as it is advanced transversely. In turn, these advantages also reduce the amount of transverse force that is required to be applied to side 10S1 in order to mover the implant transversely, thereby greatly reducing the risk of breaking the implant body 10, particularly when it is made of polymer.

Once the first implant 10 has been inserted substantially straight through the port 400, in a substantially posterior to anterior direction and orientation, as shown in FIG. 5A, the inserter instrument 100 is detached from the first implant 10 by unscrewing the threaded rod 110 from the threaded bore 24 (using actuator 112) and withdrawing the inserter instrument from the surgical space.

Figure 5B:
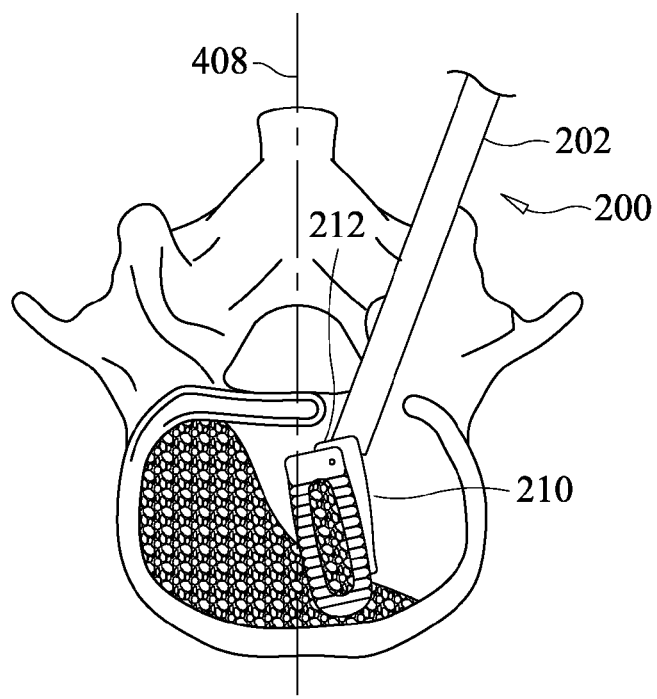

Next, the working end of first side impactor instrument 200 is inserted through port 400 and is manipulated to engage first foot 210 in contact with side 10S1 while second foot 212 contacts the proximal end 10P of the first implant 10, as shown in FIG. 5B. Instrument 200 is then used to drive first implant 10 transversely toward the median of the disc space and potentially at least partially across the median 408 of the disc space 406, as shown in FIG. 5B. The first side impactor instrument 200 is then withdrawn from contact with the first implant 10 and from the surgical working space.

Figure 5C:
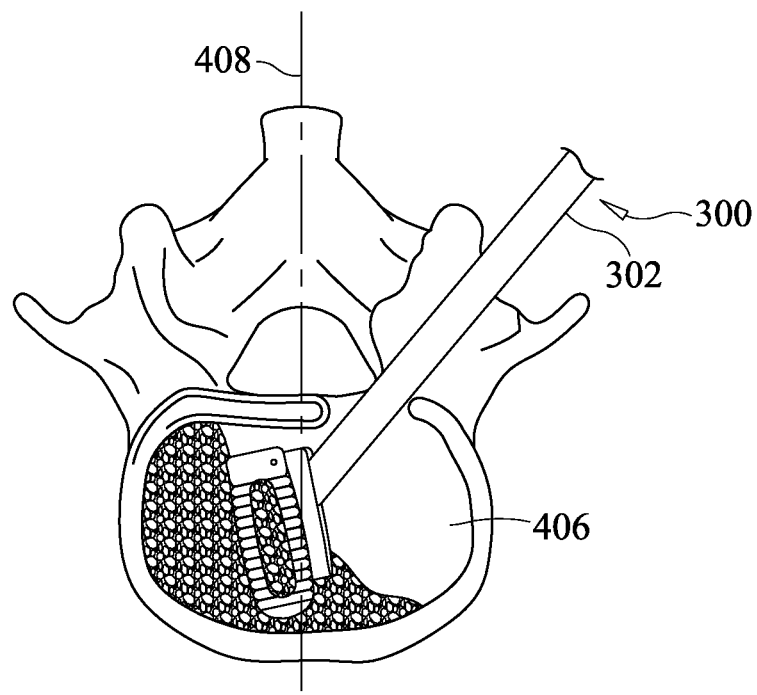

The second side impactor instrument 300 is then inserted, working end first, through the port 400 and into the disc space. Knob 312 is inserted into and engaged with the proximal most opening 28 on side 10S1 and foot 310 is engaged in contact with side 10S1. Instrument 300 is the manipulated to further transversely drive first implant 10 into the desired position on the opposite side (opposite to the side of the port 400 leading into the first side of the disc space) of the disc space 406, as shown in FIG. 5C. Because the working end of instrument 300 is oriented at a greater angle to the longitudinal axis of the instrument 300, relative to the angle that the working end of instrument 200 is angled to the longitudinal axis of instrument 200, this enables the surgeon to manipulate the shaft 302 at a greater angle relative to the anterior-posterior direction, which is required in order to translate the first implant 10 further away from the median of the disk space, as can be seen by comparing the angle of shaft 302 and median 408 in FIG. 5C, to the angle of shaft 202 and median 408 in FIG. 5B. Alternative to the procedure described above, the placement of the first implant 10 can be performed without use of first side impactor instrument 200, i.e., by using instrument 300 immediately after placement by instrument 100. However, this alternative procedure would be more cumbersome than that performed using all three instruments 100, 200, 300.

Once the first implant 10 has been positioned on the side of the disc space 406 opposite to the side that it was initially inserted into and is oriented as desired, instrument 300 is removed from contact with first implant 10 and withdrawn from the surgical space. Before implanting the second implant, the anterior aspect of the disc space on the side of the port 400 can be further filled with graft material 402 as desired. Also, the space between the first implant 10 and the location where the second implant 10 is to be place can be filled with graft material 402 at this time.

Next, the second implant 10 is inserted using an inserter instrument in the manner described above. Importantly however, the second implant 10 has an orientation that is flipped relative to the first implant. Specifically, prior to insertion, it must be confirmed that the side 10S2 having relatively less height: is oriented so that it is lateral of the side 10S1 that is non-tapered and has greater height. This orientation is better conforms the second implant 10 to the concavity of the end plates of the vertebrae that contact the implant on both top and bottom. Likewise, since the shorter side 10S2 of the first implant 10 has now been positioned lateral to the taller side 10S1, it also better conforms to the concavity of the end plates of the vertebrae, and both implants 10, 10 therefore exhibit improved load sharing, relative to other implants that have both sides of equal height. Also, in the anterior-posterior direction, the top and bottom surfaces 10T, 10B of both implants 10 are convex, and thereby better conform to the concavity of the respective endplates that they support, which also results in improved distribution of load over the implants 10.

Figure 5D:
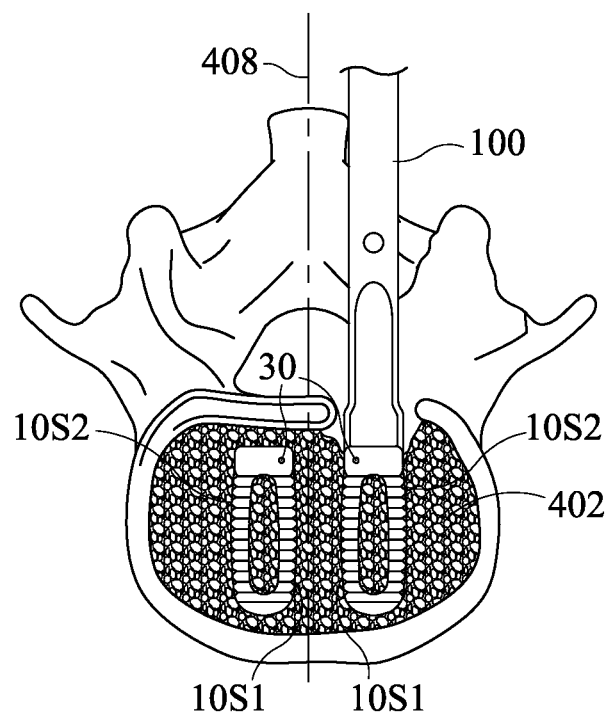

Once the second implant 10 has been positioned as desired, like shown in FIG. 5D, instrument 100 is detached from the second implant 10 and removed from the surgical space, in the same manner as described above with regard to the first implant 10. Additional graft material 402 can be placed in between the two implants 10, as it is easier to pack graft material 402 in this area after the second implant 10 is placed. This gives additional stability to the construct and will encourage a honeycomb of bone graft healing.

Figure 5E:
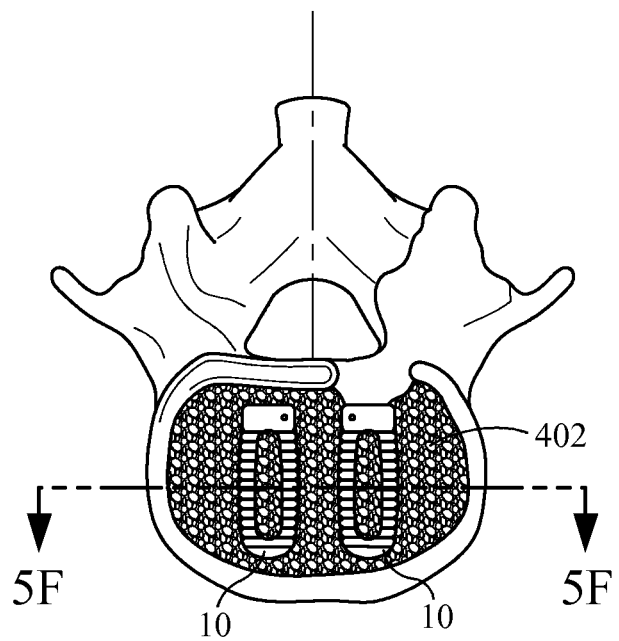
Figure 5F:
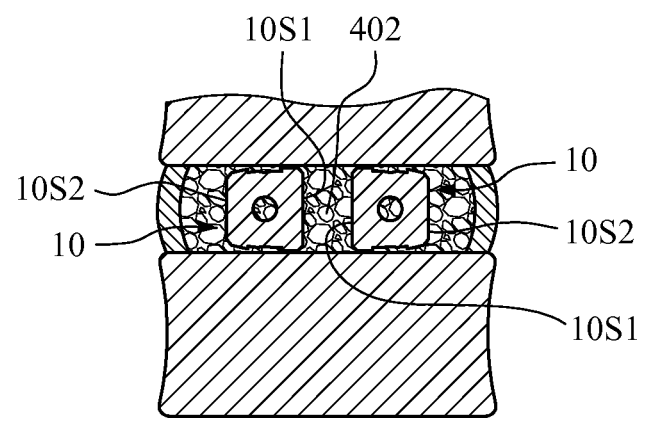

FIG. 5E shows both implants 10 in their desired positions and orientation, after completion of any additional graft material 402 packing and after removal of all instruments. FIG. 5F is a cross-sectional view of FIG. 5E taken along 5F-5F, and shows that the taller sides 10S1 are placed medially, while the shorter sides 10S2 are placed laterally relative to the respective taller sides 10S1. The positions of the implants can be checked at this time to ensure they are as desired, such as by using an image intensifier and/or fluoroscopy. When the positions are confirmed as satisfactory, the distraction of the vertebrae is removed and final compression is applied according to known techniques. Once compression is complete, final tightening of pedicle screws is performed, also according to known techniques, and the patient is closed according to known techniques.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A unilateral method of inserting first and second interbody implants in performance of posterior lumbar interbody fusion, said method comprising:
creating an interbody port posteriorly on one side of a spinal column, while maintaining structures of the spinal column and a lumbar musculoligamentous complex on an opposite side of the spinal column relative to the port, intact;
removing disc material through an incision in an annulus fibrosus of a disc in communication with the port and through the port to leave a disc space remaining;
inserting the first interbody implant through the port and into the disc space, wherein the first interbody implant has a first distal end portion, a first proximal end portion and first and second sides extending between said first distal end portion and said first proximal end portion, wherein a height of said first interbody implant on said first side is less than a height of said interbody implant on said second side, and wherein said first interbody implant is inserted such that said first side is medially placed and said second side is laterally placed on a first side of the disc space;
driving the first interbody implant from a location in the disc space on the first side, over a median of the disc space and into a position in the disc space on a second side of the disc space, such that, as a result, the first side of the first interbody implant is laterally placed and the second side of the first interbody implant is medially placed on the second side of the disc space; and
inserting the second interbody implant through the port and into the disc space on the first side of the disc space, wherein the second interbody implant has a second distal end portion, a second proximal end portion and third and fourth sides extending between said second distal end portion and said second proximal end portion, wherein a height of said second interbody implant on said third side is less than a height of said second interbody implant on said fourth side, and wherein said second interbody implant is inserted such that said fourth side is medially placed and said third side is laterally placed on a first side of the disc space.

2. The method of claim 1, wherein said first and second interbody implants are each substantially trapezoidal-shaped in a cross section taken normal to a longitudinal axis thereof.

3. The method of claim 1, further comprising distracting the disc space prior to said inserting steps, by applying distraction forces to vertebrae adjacent the disc space.

4. The method of claim 1, further comprising packing each said interbody implant, prior to said inserting, with a material that encourages bone ingrowth.

5. The method of claim 1, further comprising packing a space between said first and second interbody implants, after insertion thereof, to encourage a honeycomb pattern of bone ingrowth into the disc space, wherein said first and second interbody implants do not contact one another.

6. The method of claim 1, wherein said first interbody implant is located entirely on the second side of the disc space and said second interbody implant is located entirely on the first side of the disc space.

7. The method of claim 1, wherein said first and second interbody implants are spaced apart and do not contact one another when in final implantation locations.

8. The method of claim 1, wherein said first and second interbody implants are spaced apart and do not contact one another when in final implantation locations.

9. The method of claim 1, wherein said first and second body implants comprises first and second longitudinal axes, respectively, said first and second body implants being implanted such that said first and second longitudinal axes are substantially parallel with an anterior-posterior axis of the spinal column.

10. A unilateral method of inserting first and second interbody implants in performance of posterior lumbar interbody fusion, said method comprising:
creating an interbody port posteriorly on one side of a spinal column, while maintaining structures of the spinal column and a lumbar musculoligamentous complex on an opposite side of the spinal column relative to the port, intact;
removing disc material through an incision in an annulus fibrosus of a disc in communication with the port and through the port to leave a disc space remaining;
inserting the first interbody implant through the port and into the disc space, wherein the first interbody implant has a first distal end portion, a first proximal end portion and first and second sides extending between said first distal end portion and said first proximal end portion, wherein a height of said first interbody implant on said first side is less than a height of said interbody implant on said second side, and wherein said first interbody implant is inserted such that said first side is medially placed and said second side is laterally placed on a first side of the disc space;
translating the first interbody implant from a location in the disc space on the first side, over a median of the disc space and into a position in the disc space on a second side of the disc space, such that, as a result, an entirety of the first side of the first interbody implant is laterally placed and an entirety of the second side of the first interbody implant is medially placed on the second side of the disc space; and
inserting the second interbody implant through the port and into the disc space on the first side of the disc space, wherein the second interbody implant has a second distal end portion, a second proximal end portion and third and fourth sides extending between said second distal end portion and said second proximal end portion, wherein a height of said second interbody implant on said third side is less than a height of said second interbody implant on said fourth side, and wherein said second interbody implant is inserted such that an entirety of said fourth side is medially placed and an entirety of said third side is laterally placed on a first side of the disc space.

11. The method of claim 10, further comprising providing a space between said first side and said fourth side to facilitate a honeycomb formation of fusion, and wherein said first and second interbody implants do not contact one another.

12. The method of claim 11, further comprising packing said space with a graft material.

* * * * *